United States Patent [19]
Murphy

[11] Patent Number: 5,205,912
[45] Date of Patent: Apr. 27, 1993

[54] CONVERSION OF METHANE USING PULSED MICROWAVE RADIATION

[75] Inventor: William J. Murphy, Brights Grove, Canada

[73] Assignee: Exxon Research & Engineering Company, Florham Park, N.J.

[21] Appl. No.: 858,917

[22] Filed: Mar. 27, 1992

Related U.S. Application Data

[63] Continuation of Ser. No. 686,333, Apr. 16, 1991, abandoned, which is a continuation of Ser. No. 457,426, Dec. 27, 1989, abandoned.

[51] Int. Cl.$^5$ ............................................. C07C 1/00
[52] U.S. Cl. ........................... 204/157.15; 204/157.43; 204/170; 204/171
[58] Field of Search ................ 204/157.15, 157.6, 168, 204/170, 172; 208/106–107, 133, 142; 585/648, 953

[56] References Cited

U.S. PATENT DOCUMENTS

| | | | |
|---|---|---|---|
| 4,474,625 | 10/1984 | Cohen et al. | 148/1.5 |
| 4,574,038 | 3/1986 | Wan | 204/157.15 |
| 4,721,828 | 1/1988 | Withers | 585/500 |
| 4,919,974 | 4/1990 | McCune et al. | 427/244 |
| 4,975,164 | 12/1990 | Ravella et al. | 204/156 |
| 5,015,349 | 5/1991 | Suib et al. | 204/168 |

OTHER PUBLICATIONS

Gasner et al., "Microwave and conventional pyrolysis of a bituminous coal", Chem. Abs. 106:7281h (1987).

Primary Examiner—John Niebling
Assistant Examiner—C. Delacroix-Muirheid
Attorney, Agent, or Firm—John W. Ditsler; James H. Takemoto

[57] ABSTRACT

Methane can be effectively converted to acetylene, ethylene, and hydrogen by subjecting the methane to pulsed microwave radiation in the presence of at least one plasma initiator that is capable of initiating an electric discharge in an electromagnetic field.

14 Claims, 6 Drawing Sheets

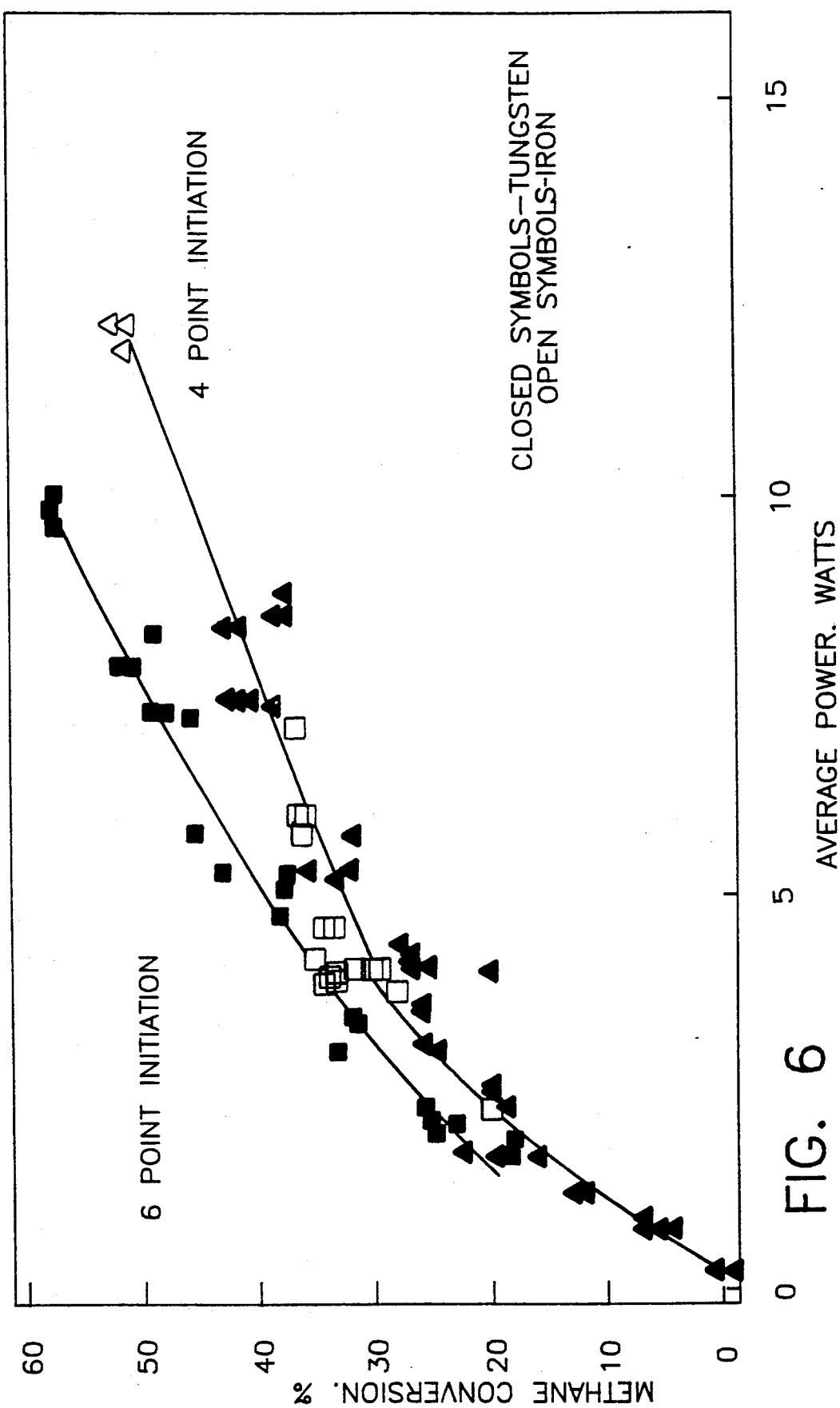

CONVERSION OF METHANE USING PULSED MICROWAVE RADIATION

This is a continuation of application Ser. No. 686,333, filed Apr. 16, 1991 now abandoned which is a continuation of Ser. No. 457,426 filed Dec. 27, 1989 now abandoned.

BACKGROUND OF THE INVENTION

1. Field of the Invention

This invention relates to a method for converting methane to higher molecular weight hydrocarbons and hydrogen using pulse microwave radiation.

2. Description of Related Art

Microwave energy has been used to convert methane to other hydrocarbons. For example, U.S. Pat. No. 4,574,038 discloses that methane can be converted to ethylene and hydrogen in a batch process at pressures of from 0.3 to 1 atmosphere by subjecting the methane to microwave radiation in the presence of a metal powder catalyst. Another example of methane conversion using microwave energy is U.S. Pat. No. 3,663,394.

However, neither patent suggests the particular methane conversion process described below.

SUMMARY OF THE INVENTION

This invention concerns the synthesis of higher molecular weight hydrocarbons and hydrogen from a methane source. More specifically, methane can be converted into higher molecular weight hydrocarbons (e.g. acetylene and ethylene) and hydrogen by irradiating the methane with pulsed microwave radiation in the presence of at least one elongated plasma initiator that is capable of initiating an electric discharge in an electromagnetic field. In a preferred embodiment, molecular hydrogen will be present initially and the plasma initiator will comprise a plurality of elongated metal wire segments arranged in close proximity to one another.

BRIEF DESCRIPTION OF THE DRAWINGS

FIG. 6 is a graph of methane conversion versus average power which shows the effect of the number of plasma initiators on methane conversion.

DETAILED DESCRIPTION OF THE INVENTION

Figure 1:
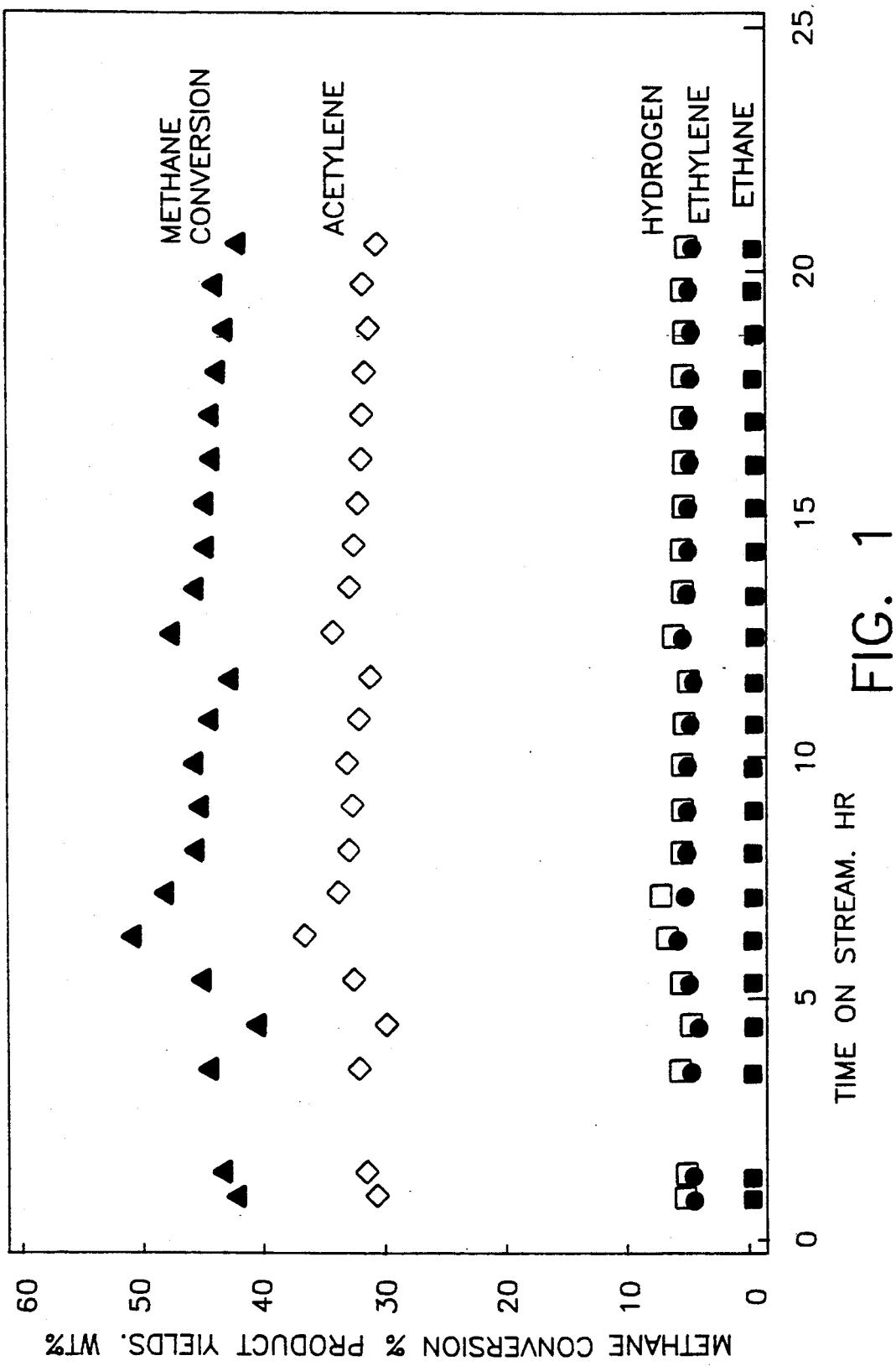
FIG. 1 is a graph of methane conversion and product yields versus time.

This invention requires the presence of methane, at least one elongated plasma initiator capable of initiating an electric discharge in an electromagnetic field, and a source of pulsed microwave energy.

The methane may be pure or mixed with other hydrocarbons (e.g. as in natural gas). Non-hydrocarbons (e.g. $CO_2$, $H_2S$, $N_2$, etc.) may be present as well.

The plasma initiator may be essentially any material capable of accumulating an electric charge when placed in an electromagnetic field and then dissipating the charge (or initiating an electric discharge), for example, by ionizing a gas environment. This includes metal initiators, non-metal initiators (including semi-conductors), and composites of metal and non-metal initiators. As used herein, "composite" is meant to include mixtures (or combinations) of metals and non-metals. Examples of suitable metal initiators are tungsten, iron, nickel, copper, their alloys, or mixtures thereof. Preferred metal initiators are tungsten, iron, or mixtures thereof, with iron being particularly preferred. Examples of suitable non-metal initiators include carbon, alumina, manganese dioxide, magnetite, nickel oxide (e.g. NiO), iron oxide (e.g. $Fe_3O_4$), calcium aluminate, cobalt oxide, chromium nitride, iron sulfide (e.g. $FeS_2$, $Fe_{1-x}S$), copper sulfide (e.g. $CuS_2$), or mixtures thereof. Calcium aluminate, carbon, iron oxide, or their mixtures are preferred non-metal initiators, with carbon being particularly preferred. Silica is not a suitable non-metal initiator. However, silica composited with a metal initiator or another non-metal initiator would be a suitable plasma initiator.

Although methane conversion can be effected using only one plasma initiator, conversion is enhanced if more than one (e.g., 6 or more) plasma initiators are used. Preferably, a plurality of plasma initiators are used. Most preferably, the plasma initiator will comprise a plurality of metal wire segments. Each plasma initiator should be of at least a minimum length that is sufficient to initiate an electric discharge when placed in an electromagnetic field. However, the precise minimum length of each initiator may vary with the frequency of the microwave source as well as the geometry of the reaction zone and of the initiator.

If more than one plasma initiator is used, a minimum distance should be maintained between each initiator to facilitate dissipation of the electric charge. However, the minimum distance will vary depending upon the frequency of the microwave source. As an example, the minimum distance should be at least about 0.25 cm, preferably at least about 0.5 cm, for a frequency of 2.45 GHz.

The plasma initiators should be elongated, but may be formed, combined, or bent in any convenient shape (e.g., straight, helix, spiral, and the like). Preferably, the initiators should be formed such that there are points or sharp edges at the ends or on the surface of the initiators.

The plasma initiators may be stationary within the reaction zone or they may be in motion. The motion can result from the initiators being fluidized by a gas (e.g. the methane feedstock) or by other means (e.g. an external magnetic field gradient).

The frequency of the microwave source can vary broadly. Typically, the microwave energy will have a frequency of at least 0.3 GHz, with frequencies centered around 0.915, 2.45, 5.80, or 22.0 GHz presently being preferred in North America; particularly frequencies centered around 0.915, 2.45, or 5.80 GHz; especially frequencies centered around 0.915 or 2.45 GHz.

The microwave energy used in this invention is pulsed, which allows better temperature control of the plasma initiators to optimize energy use. The duration of on-time pulses can vary broadly, but typically will range from about 1 nanosecond to about 20 seconds, preferably from about 1 millisecond to about 10 seconds, and most preferably from about 0.01 to about 0.2 seconds. The duration of off-time rests can vary broadly as well, but typically will range from about 1 nanosecond to about 100 seconds, preferably from about 0.003 to about 60 seconds, and most preferably from about 0.3 to about 5 seconds.

Molecular hydrogen should also be present in the reaction zone to maintain the activity of the plasma initiators for methane conversion. The amount of hydrogen in the reaction zone during conversion should be sufficient to maintain a mole ratio of methane to hydrogen greater than 1:1, preferably at least 1:1.5, more preferably at least 1:2, and most preferably at least 1:4. Although some methane conversion may occur at mole ratios of 1:1 or less, greater conversion will be obtained at higher mole ratios because hydrogen tends to reduce or inhibit the formation of carbonaceous deposits on the plasma initiators. While not wishing to be bound by any particular theory, it is believed that at lower mole ratios, greater amounts of carbonaceous deposits accumulate on the initiators and inhibit their ability to ionize the gas environment.

Although extraneous molecular hydrogen need not be added, if a sufficient amount of hydrogen is not present initially in the reaction zone, the initiators will deactivate until a sufficient amount of hydrogen is present (or has accumulated, for example, by recycling the hydrogen formed during conversion) to retard deactivation and maintain the mole ratio at a level that will stabilize the methane conversion at a particular level. This so-called induction period results in an initial loss of initiator activity and, hence, a lower level of methane conversion than if hydrogen had been present initially. To avoid this undesirable loss of conversion, it is preferred to add extraneous hydrogen to the reaction zone initially to minimize or prevent the initial loss of initiator activity and methane conversion. This extraneous hydrogen may be pure or in a mixture with other gases (e.g. as from a naphtha reformer) and may be added to the reaction zone separately or in mixture with the methane.

This invention can be practiced at any convenient temperature and pressure, including ambient conditions. However, the relative amounts of acetylene and ethylene formed will vary with pressure, with a greater amount of ethylene being formed at elevated pressures (i.e., pressures greater than atmospheric). In addition to acetylene and ethylene, this invention also contemplates the formation of aromatic compounds such as benzene, alkyl benzenes, xylenes, and the like.

This invention will be further understood by reference to the following Examples which are not intended to restrict the scope of the appended claims.

EXAMPLE 1

Conversion of Methane

A methane/hydrogen mixture (1:4 mole ratio) flowing at 25 ml/min (milliliters/min) at atmospheric pressure was contacted with 1.5 gm of tungsten wire (about 0.03 inches in diameter and cut into 45 mm lengths) in a reactor fabricated from WR430 waveguide bounded by quartz plate glass windows and positioned approximately one-quarter waveguide wavelength from a short circuit plate. The reactor was irradiated with microwave radiation centered at a 2.45 GHz frequency and pulsed in an on/off cycle (0.14 seconds on in a total of 3.5 seconds) with an average power of 3.6 watts. Methane conversion was calculated according to the following equation:

$$\% \text{ Methane Conversion} = \left[1 - \frac{\text{wt. \% methane in the products}}{\text{wt. \% methane in the feed}}\right] \times 100$$

The methane conversion obtained is shown in FIG. 1 as a function of time. FIG. 1 also shows that the primary hydrocarbon products produced were acetylene (an average of 33.6 wt. %) and ethylene (an average of 5.6 wt. %). Hydrogen (an average of 6.1 wt. %) and small amount of ethane (an average of 0.25 wt. %) were also produced.

EXAMPLE 2

Effect of $CH_4/H_2$ Mole Ratio on Methane Conversion

Figure 2:
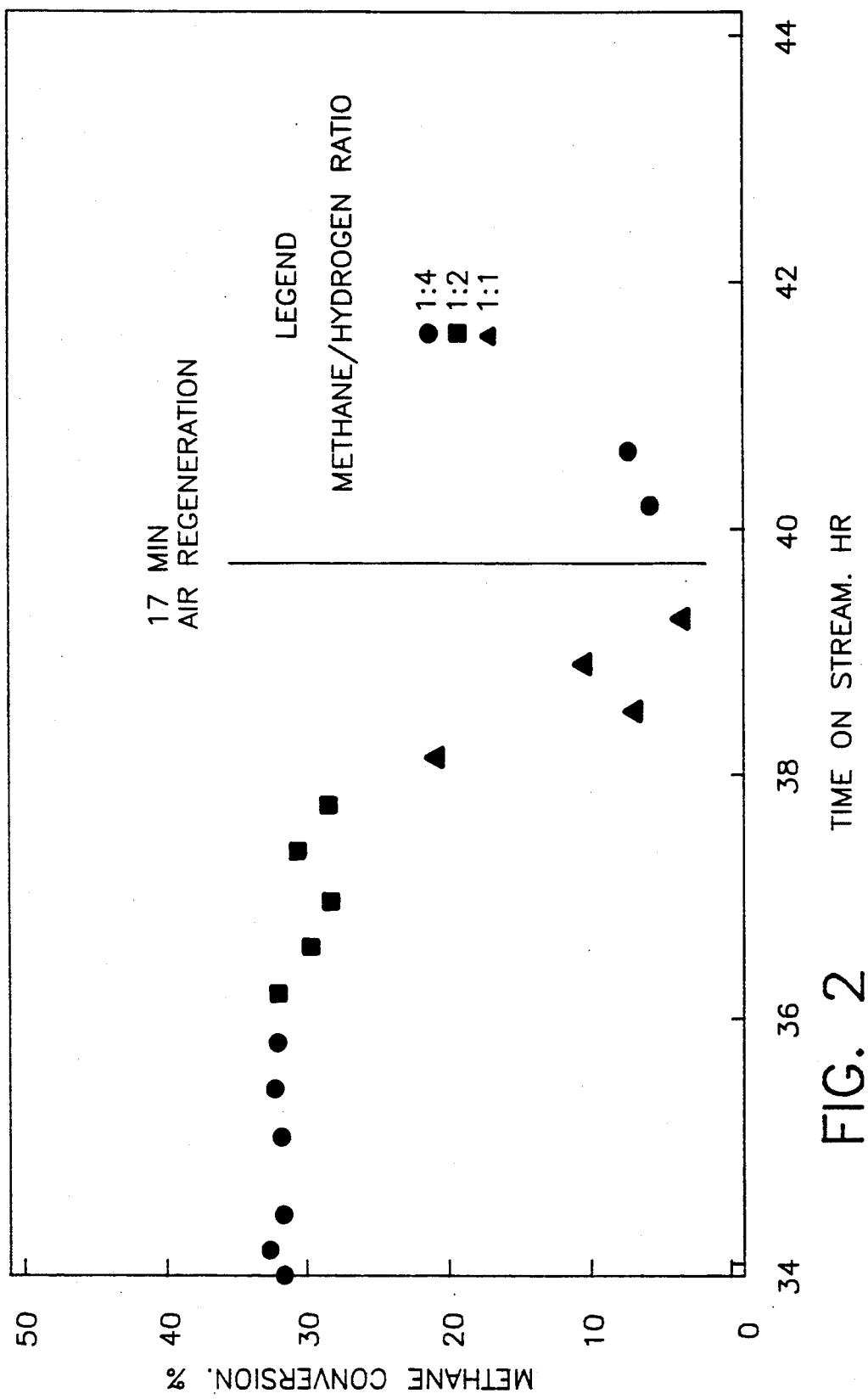
FIG. 2 is a graph of methane conversion versus time which shows the effect of $CH_4/H_2$ mole ratio on methane conversion.

Using the apparatus and procedure of Example 1 (except that 2.9 gm of iron wire was used and the average power ranged from 7.5 to 10 watts), the methane/hydrogen mole ratio was decreased from 1:4 to 1:1. The results of this test (as illustrated in FIG. 2) show that a reduction of the methane/hydrogen mole ratio from 1:4 to 1:2 had little effect on methane conversion. However, a further reduction to 1:1 resulted in a significant decrease in methane conversion. This decrease proved to be irreversible as shown by the further contact with the methane/hydrogen mixture (1:4 mole ratio) following 17 minutes of regeneration in air.

EXAMPLE 3

Effect of Various Plasma Initiators on Methane Conversion

Figure 3:
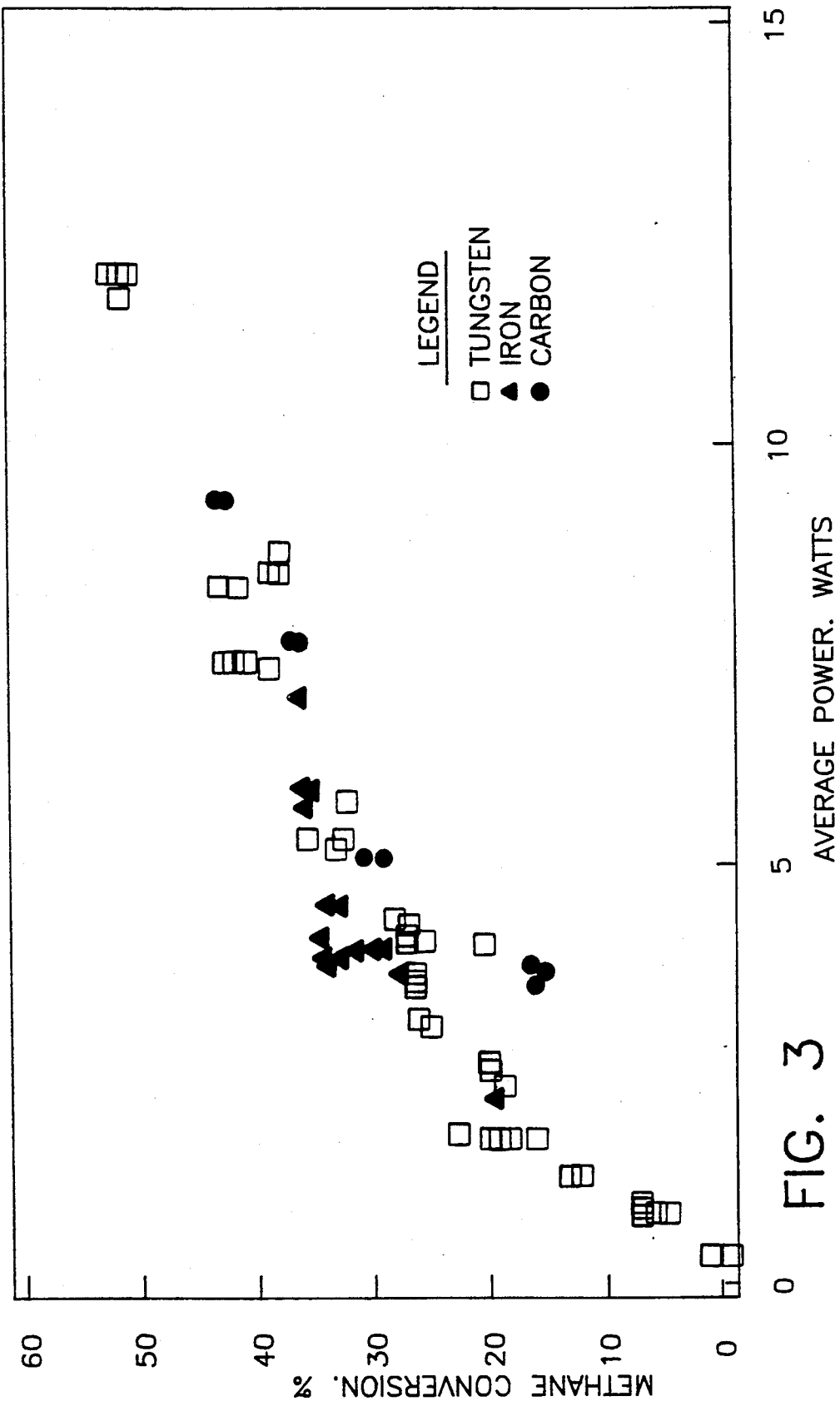
FIG. 3 is a graph of methane conversion versus average power which shows that various plasma initiators are effective for methane conversion.

Using the apparatus and procedure of Example 1, various plasma initiators were tested for their effectiveness in converting methane. The results of these tests (as illustrated in FIG. 3) show that tungsten, iron, or carbon (in the form of fibers) can be used without any adverse effect on methane conversion. However, in a companion experiment using silica fibers as the plasma initiator, no methane conversion was obtained.

EXAMPLE 4

Effect of Elevated Pressure on Product Distribution

Using the apparatus and procedure of Example 1 (except that the methane/hydrogen mole ratio ranged from 1:1 to 1:11 and methane flow rates ranged from 5 to 20 ml/min), tests were made to determine the effect of pressure on product selectivity. The results of these tests are shown in FIG. 4 at various apparent contact times, which is defined as follows:

$$\text{Apparent Contact Time (sec)} = \frac{3600 \times FMW \times P}{1206 \times T \times CD \times WHSV \times (H_2:\text{Feed}) + 1)}$$

where
FMW = Average molecular weight of the hydrocarbon feed
P = Pressure, psia
T = Arbitrarily set at 373° K.
CD = Initiator bulk density, g/cc
$H_2$:Feed = Hydrogen to methane mole ratio
WHSV = Weight hourly space velocity, w/w/h 3600=Conversion from hours to seconds 1206=Gas constant in $(cm^3)(psia)/(gm\ mole)(°K.)$.

Figure 4:
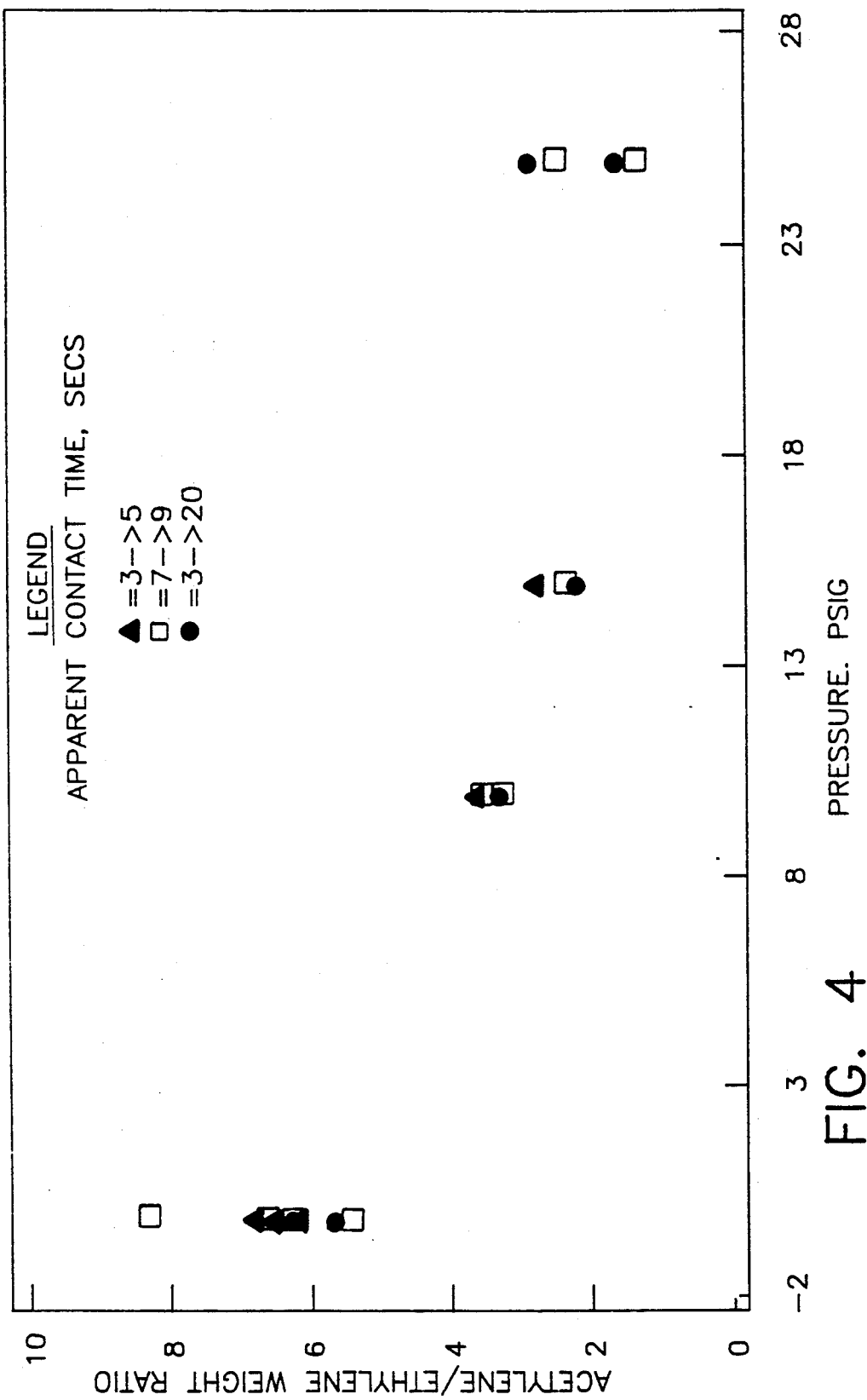
FIG. 4 is a graph of acetylene/ethylene weight ratio versus pressure which shows the effect of elevated pressure on product distribution.

The data in FIG. 4 show that the product distribution is relatively insensitive to apparent contact time, but increasing pressure favors the formation of ethylene rather than acetylene. Thus, this invention also contemplates the products from methane conversion being primarily ethylene and hydrogen at elevated pressures.

EXAMPLE 5

Effect of Plasma Initiator Proximity on Methane Conversion

Figure 5:
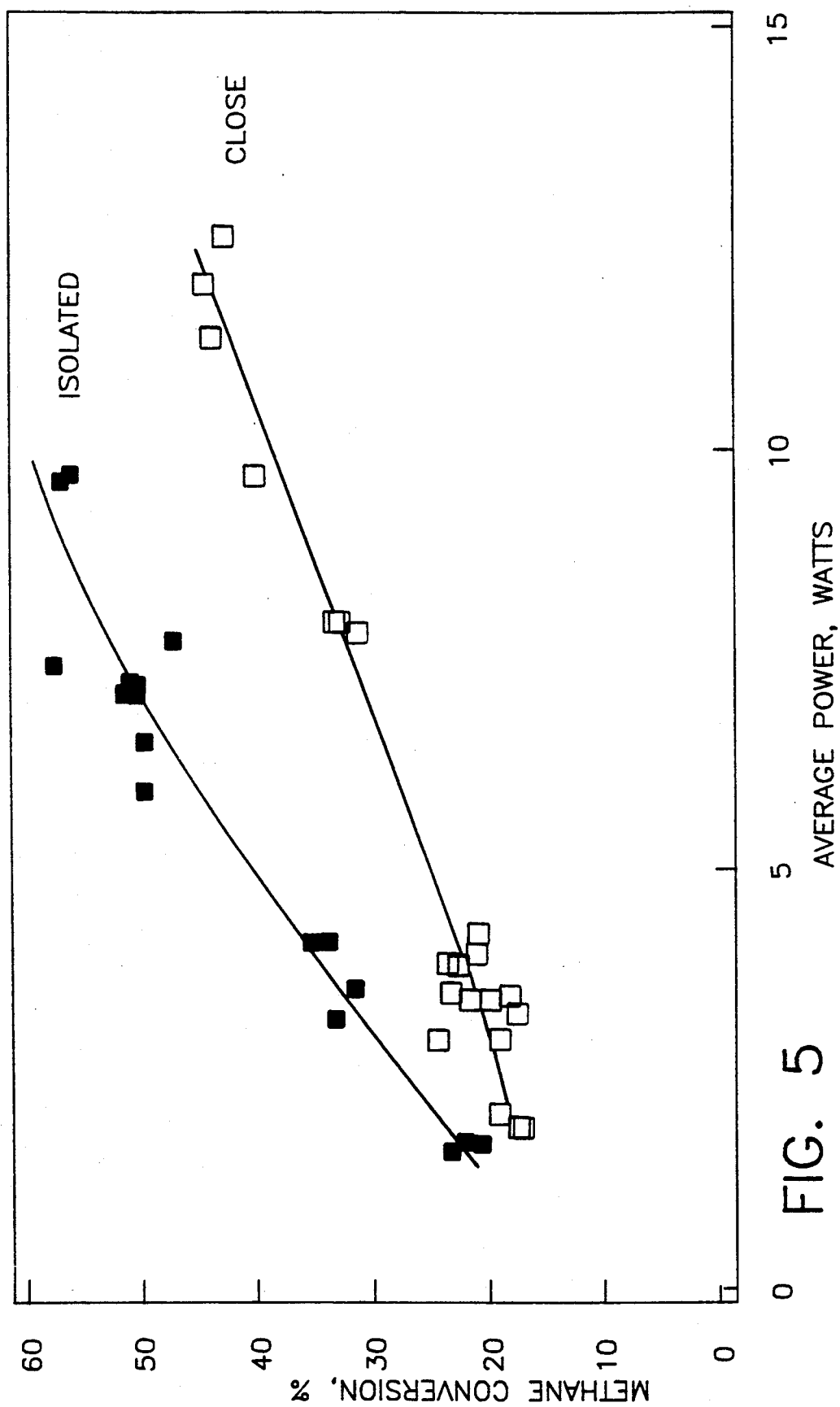
FIG. 5 is a graph of methane conversion versus average power which shows that the proximity of the plasma initiators affects methane conversion.

The apparatus and procedure of Example 1 was used to determine the effect of the proximity (or interpoint distance) of plasma initiators on methane conversion. In this example, the distance between plasma initiators was varied from about 0.5 cm (close) to about 1.0 cm (isolated). The results obtained (as illustrated FIG. 5) show that increased methane conversion is obtained when the initiators are isolated.

EXAMPLE 6

Metal Powders and Filings are Ineffective for Methane Conversion

A methane/hydrogen (1:4.2 mole ratio) mixture flowing at 12.9 ml/min at about atmospheric pressure was introduced into a quartz reactor and contacted with 0.2 g of nickel powder (from Alpha Products) having a 1.0 micron particle size. The reactor was irradiated with microwave radiation centered at 2.45 GHz frequency having 700 watts of power pulsed in an 50/50 on/off cycle, the cycle length of which was about 22 sec. The product stream was analyzed by gas chromatography and showed essentially no conversion of methane to acetylene and ethylene.

Following the same procedure, another experiment using a methane/hydrogen (1:4.1 mole ratio) mixture flowing at 11.2 ml/min and iron powder (Fisher I 60 grade) gave the same result.

Another experiment using 0.4 g iron filings (about 40 mesh) and the same conditions as the iron powder again gave the same result.

The data in this example show that metal powders and filings are ineffective initiators for methane conversion.

EXAMPLE 7

Effect of Number of Plasma Initiators on Methane Conversion

The apparatus and procedure of Example 1 was used to determine the effect of the number of plasma initiators on methane conversion, except that 3.0 g of tungsten wire was used. The results obtained (as illustrated in FIG. 6) show that higher methane conversion is obtained with 6 rather than 4 plasma initiators.

What is claimed is:

1. A method for converting methane to acetylene, ethylene, and hydrogen which comprises
   (a) introducing methane into a reaction zone that contains at least one elongated plasma initiator capable of initiating an electric discharge in an electromagnetic field, and
   (b) subjecting the methane and plasma initiator to pulsed microwave radiation, thereby initiating an electric discharge, ionizing the methane in the reaction zone, and converting at least a portion of the methane to acetylene, ethylene, and hydrogen.

2. The method of claim 1 wherein the plasma initiator is a metal.

3. The method of claim 2 wherein the metal is tungsten, iron, nickel, copper, their alloys, or mixtures thereof.

4. The method of claim 3 wherein the metal is tungsten, iron, or mixtures thereof.

5. The method of claim 1 wherein the plasma initiator is a non-metal other than silica.

6. The method of claim 5 wherein the non-metal is calcium aluminate, carbon, iron oxide, or mixtures thereof.

7. The method of claim 1 wherein the plasma initiator is a composite of a metal initiator and a non-metal initiator.

8. A method for converting methane, to acetylene, ethylene, and hydrogen which comprises
   (a) introducing methane into a reaction zone which contains a plurality of metal wires capable of initiating an electric discharge in an electromagnetic field, and
   (b) subjecting the methane and metal wires to pulsed microwave radiation having a frequency of at least 0.3 GHz, thereby initiating an electric discharge, ionizing the methane in the reaction zone, and converting at least a portion of the methane to acetylene, ethylene, and hydrogen, wherein the mole ratio of methane to hydrogen is greater than 1:1 during conversion.

9. The method of claim 8 wherein the metal is tungsten, iron, nickel, copper, their alloys, or mixtures thereof.

10. The method of claim 9 wherein the metal is tungsten, iron, or mixtures thereof.

11. The method of claim 8 wherein the mole ratio of methane to hydrogen is at lest 1:2.

12. The method of claim 8 wherein at least one aromatic compound is formed during the methane conversion.

13. A method for converting methane to primarily ethylene and hydrogen which comprises
   (a) introducing methane into a reaction zone that contains at least one elongated plasma initiator capable of initiating an electric discharge in an electromagnetic field, and
   (b) subjecting the methane and plasma initiator to pulsed microwave radiation, thereby initiating an electric discharge, ionizing the methane in the reaction zone, and converting at least a portion of the methane to primarily ethylene and hydrogen.

14. The method of claim 11 wherein the mole ratio of methane to hydrogen is at least 1:4 during conversion.

* * * * *